United States Patent
Ege (12)

(10) Patent No.: US 6,284,000 B1
(45) Date of Patent: Sep. 4, 2001

(54) ANATOMIC REPLACEMENT PROSTHESIS SYSTEM IN THE HAND AND WRIST

(76) Inventor: Ahmet Ege, Inönü Cad. 166, Sok. No:2/19, Hatay-Izmir (TR), 35360

( * ) Notice: Subject to any disclaimer, the term of this patent is extended or adjusted under 35 U.S.C. 154(b) by 0 days.

(21) Appl. No.: 09/125,898

(22) PCT Filed: Feb. 20, 1997

(86) PCT No.: PCT/TR97/00004

§ 371 Date: Aug. 27, 1998

§ 102(e) Date: Aug. 27, 1998

(87) PCT Pub. No.: WO97/31593

PCT Pub. Date: Sep. 4, 1997

(30) Foreign Application Priority Data

Feb. 29, 1996 (TR) .................................................. 96/00163

(51) Int. Cl.[7] .................................................................. A61F 2/42
(52) U.S. Cl. .................................... 623/21.11; 623/21.13; 623/21.16
(58) Field of Search ........................... 623/21.11, 21.12, 623/21.13, 21.14, 21.15, 21.16, 21.17

(56) References Cited

U.S. PATENT DOCUMENTS

| | | | |
|---|---|---|---|
| 4,259,752 | * | 4/1981 | Taleisnik ............................ 623/21.11 |
| 4,352,212 | * | 10/1982 | Greene et al. ..................... 623/21.11 |
| 4,645,505 | | 2/1987 | Swanson . |
| 4,936,854 | | 6/1990 | Swanson . |
| 5,314,485 | * | 5/1994 | Judet ................................. 623/21.11 |
| 5,413,609 | | 5/1995 | Nicol et al. . |
| 5,458,646 | | 10/1995 | Giachino . |
| 5,702,469 | * | 12/1997 | Whipple et al. ....................... 623/21 |
| 5,702,471 | * | 12/1997 | Grundei et al. ................... 623/21.11 |
| 5,766,258 | * | 6/1998 | Simmen ................................. 623/21 |
| 5,782,926 | * | 7/1998 | Lamprecht ............................ 623/21 |

FOREIGN PATENT DOCUMENTS

| | | |
|---|---|---|
| 0 607 749 | 7/1994 | (EP) . |
| 0 198 586 | 10/1996 | (EP) . |
| 2 673 100 | 8/1992 | (FR) . |
| 2 269 752 | 2/1994 | (GB) . |

\* cited by examiner

Primary Examiner—David H. Willse
Assistant Examiner—Suzette J. Jackson
(74) Attorney, Agent, or Firm—Nixon & Vanderhye P.C.

(57) ABSTRACT

A prosthesis system for partial or total articular surface replacement includes a tail module having one or more grooves at one end thereof and a first ball joint component at an opposite end thereof; an articular module, a portion of which has an anatomic shape of a distal radial articular surface, another portion of which is provided with a second ball joint component; and a collar module interposed between the tail module and the articular module, and comprising a pair of sockets adapted to receive the first and second ball joint components of the tail module and articular module

7 Claims, 1 Drawing Sheet

ANATOMIC REPLACEMENT PROSTHESIS SYSTEM IN THE HAND AND WRIST

TECHNICAL FIELD

This invention relates to wrist and hand prostheses in general, and specifically to a novel, modular hand or wrist replacement prosthesis system.

BACKGROUND AND SUMMARY OF THE INVENTION

Currently, wrist prostheses replace both radial and carpal components of the wrist joint. In such prostheses, the amount of carpal resection is quite considerable and the resultant changes in the wrist biomechanics lead to some dissatisfaction which results in limited application and delay in the timing of the operation until the joint is in a highly advanced degenerative state.

Currently, the wrist biomechanic is not very well understood, especially the kinematics of the skafoid and the lunatum which present semifree kind of movements relative to each other. However, in current practice the carpal component is either fixed to both of these bones or, applied after resection of these bones. Beyond that, in tumor cases, affecting the articular surface located in the distal radius, when trauma or a kind of rheumatoid disease spares the carpal bones, but seriously affects the articular surface of the radius, until today there has been no joint replacement system which can reconstruct only the damaged radial part of the wrist.

The current status of prosthetic applications in hand surgery can be reviewed from the last publication of operative Hand Surgery of David P. Green-(ISBN 0-443-08803-0 Churchill Livingstone Publications pages 143–187). In addition, the Journal of American Hand Surgery could be investigated.

It is obvious that all kinds of current prostheses force the surgeon inevitably to change the whole of the joint. In case of the normal carpal side cartilage, to be obligated to apply a prosthesis to the carpal side of the joint increases the risk of complication and may be regarded as "excessive treatment".

In applications relating to the total wrist prosthesis, problems with loosening seen particularly in the carpal component and the stability lost due to the wide carpal resection are still unsolved. Therefore, many surgeons keep away from total wrist prosthesis surgery and prefer artrodesis or delay surgery until extreme deformity occurs. The new concept in accordance with this invention enables the prosthetic replacement of only the damaged part of the joint (taumatic, tumoral, degenerative and so on). Likewise with the assistance of the limited replacement arthroplastie, the original biomechanic of the wrist joint is maintained and provides a sort of profilactic surgery with conservation of wrist ligaments and undamaged parts of the joint. In daily practice, the phenemenons which disturb the morphologic and functional wholeness of such as intraarticular fractures, such as giant cell tumors generally occurs within the distal radius. In such cases, arthroplastie which reconstructs only the radial part of the joint is not described. Certainly, the prosthetic material in question will be in different types according to the location and the stage of the pathology. For instance, in case of benign tumors, a design possessing a massive stem (body) to be applied with bone cement (Methilmetakrilat) is preferable. On the other hand, in a case of intraarticular fractures, the application of cementless, low profile design will be chosen to leave sufficient bone stock.

With the new concept which we have introduced here, the realization of further experimental and clinical studies and prototype designs undoubtedly will be developed. Similarly, the fact that the distal radio-ulnar is affected or not will modify the choice of required design.

Following the arthroscopic MRI and operative findings, if only the carpal bones' articular surfaces are found degenerated, the surgeon may be content with only the replacement of the degenerated surfaces. Moreover, if only a part of radial articular surface is found degenerated (Skafoid or Ulnar fossa), again the surgeon may choose limited replacement of only degenerated parts in the form of a hemi-partial prosthetic application, sparing the rest of the joint. The insertion of the radial component may either be realized by a trans- radial -stiloid approach which is not published yet, in case of distal radiovulnar joint degeneration, the Taleisnik modification approach for Kapanji procedure (resection of distal ulnar), or finally the current dorsal approach used regularly in wrist replacement arthroplastie being for hemi-partial application.

Whether TFCC (Triangular fibrocartilage complex) is intact or not, and the carpal instability added or not, may imply little modifications in the design.

In accordance with the abovementioned principles, partial surface replacement prosthetic applications are not described and realized for finger joints. Till today surgeons exhorted arthrothesis in case of introarticular fractures or benign tumors located adjacent to finger joints. Thus the joint is sacrificed, even if one of the joint surfaces is completely intact. Furthermore, only the fracture which holds one articular surface of the MP or PIP joint may imply a contraindication for revascularisation or replantation of the finger. Therefore, a simple partial surface replacement can change the outlook of the whole finger. Also in corpometacorpal an intercarpal joints, only the damaged surfaces' anatomic replacement can be used.

The surfaces of the prosthesis may be metal or plastic in nature. The surfaces be covered with plastic or other material or, as an alternative measure some chemicals may be injected in the joint space between the prosthetic material and the opposing normal articular surface.

The prosthesis can be secured by cement or not. Bone graft, porouscoated, hidroksipatit impregrinated surface, bone-ongrowth, and bone-ingrowth phenomenons may be taken into consideration when designing the prosthesis. The components of the modular prosthesis may be fabricated to facilitate assembly of the device outside of the body, or inside the body with a different of surgical approach. Arthroscopic assistance may probably be required. With the plate and the screw application, additional primary stability can be obtained. Variations of plate and screw applications can be fixed or assembled over the material.

To increase stability, the stem and the body components may be manufactured as "expansion type". In the beginning the prototype model will possess an extension screw system, but this may be modified when necessary. Distal radial articular surface inclination angle is given generally in two different plans as 23 and 11 degree. However, we have seen considerable modifications in our measurements. Ideally we anticipate matching the angle of the articular surface with the other wrist of the patient. The modular and compact system in accordance with this invention is designed to allow this accomodation. It is obvious that this prosthetic system will be applied with the help of an instrument set to provide to find the correct size, position, and the fixation of the implant. To facilitate the insertion of the prosthesis some distraction will probably be needed. Thus a kind of external fixation device will be utilized, and in addition, multiple raspes, osteotoms and specially designed insertion devices are indispensable. These instruments will be developed in experimental studies and in following days newly designed versions will be invented. Where necessary, the prosthesis can be custom made as well.

Variations allows the fixation of the prosthesis to the bone with the help of several devices.

In the stem and or the body of the prosthesis, a rectangular area to be filled with bone graft taken with a special instrument may be helpful to contribute to the stability of the device.

In the above mentioned radial styloid approach, the main concern is to protect volar and dorsal ligaments, and thus the stability of the joint. This is a new approach not described elsewhere.

Scaphoid and lunate bones articular surfaces may be reconstructed with the help of synthetic materials initially or later. In the case of the scapho-lunate rupture which is difficult to repair, a special design to address this area may be utilized.

As it is seen, with the help of the new conceptual approach to the prosthetic surgery in the hand, it will be possible to reconstruct only the limited damaged part of the wrist joint with an anatomically designed prosthetic device. Healthy parts will be left intact, and only in the case of necessity will other parts of the joint be changed to convert to total wrist prosthesis. While doing this, and to the extent possible, any of the previously applied prosthetic components will not be removed and may be expressed through the help of an analogy to modular furniture. In following designs, main details have been mentioned on the radial prosthetic component shown in approximately natural dimensions. It must be kept in mind that necessary modifications will be realized in the details.

DETAILED DESCRIPTION OF THE DRAWINGS

Figure 1:
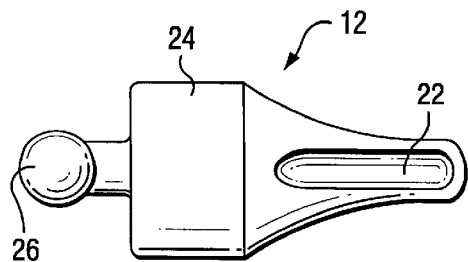
FIG. 1 is a side elevation of a tail part or module in accordance with the invention.
Figure 1A:
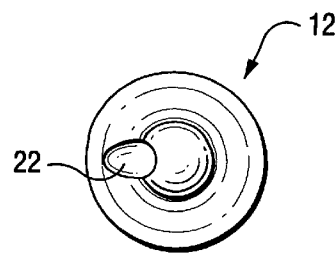
FIG. 1A is an end view of the module in FIG. 1.
Figure 2:
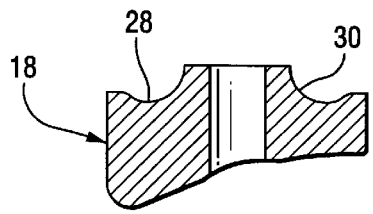
FIG. 2 is a cross section through a lower half of a collar module.
Figure 2A:
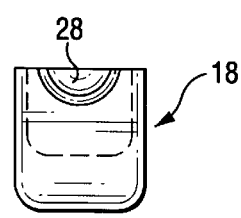
FIG. 2A is an end view of the collar module in FIG. 2.
Figure 3A:
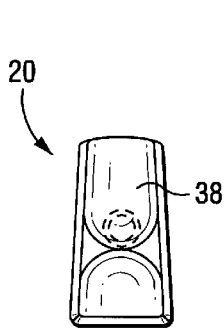
FIG. 3A is an end view of the articular module in FIG. 3.
Figure 3:
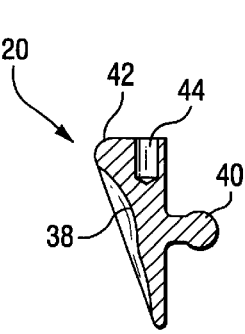
FIG. 3 is a cross section through an articular module in accordance with the invention.

With reference to FIGS. 1 through 4, the prosthesis 10 is a modular device, enabling partial or total articular surface replacement used in different pathologies of the distal radial articular surface. The prosthesis comprises three main parts, the tail part or module 12, the body part or collar module 14, formed by two similar half portions 16 and 18, and the articular surface or module 20.

The generally tapered tail part or module 12 assists in fixing the prosthesis in the medullary cavity of the bone, and includes one or more grooves or wings 22 to prevent movement after insertion and integration in the os or cement. A cylindrical portion 24 of the tail module is provided with a distal spherical protuberance or ball joint component 26 enabling it to connect with other modules of the system.

The body part or collar module 14 is comprised of the two half parts 16 and 18, each of which is provided with a pair of recesses 28, 30 and 32, 34 so that the two parts when assembled have a pair of sockets for receiving the ball joints as described further below. The two half parts 16 and 18 may be secured with the assistance of a screw 36.

The articular surface module 20 (FIG. 3) includes an articular surface 38 along with a proximal spherical protuberance or ball joint component 40. The articular surface has the anatomic shape of the distal radial articular surface and it is in harmony with the contours of the corresponding proximal carpal bones (lunate and scaphoid). The enlarged end 42 is the radial border of this modular element and may have a threaded hole 44 to manipulate with a holding device.

Figure 4:
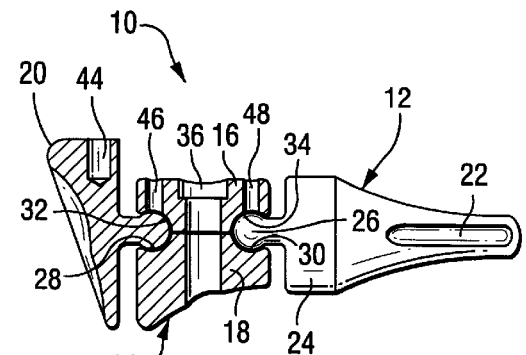
FIG. 4 is a side elevation showing the assembly of the tail module, collar module, and articular module.

With reference to FIG. 4, the articular module 20 is shown in assembled relationship at one end of the collar module 14, with the tail module 12 projecting from the other end of the collar module. The ball joint components 26 and 40 are seated within the sockets provided in the collar module 14.

Screw holes 46, 48 in each module are provided for additional stability to the assembly by fixing the ball joint components.

Figure 5:
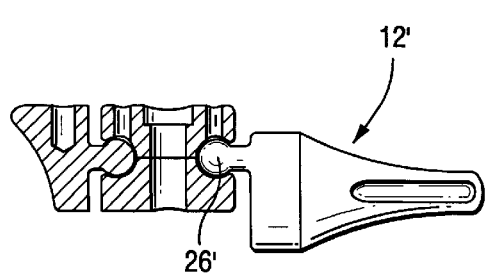
FIG. 5 illustrates an assembled prosthesis similar to that shown in FIG. 4, but with an offset ball joint.

The prosthesis can be fabricated in different sizes and may be custom made for specific patients. For example, in the case where only the scaphoid fossa of the radial articular surface is damaged, the prosthesis may be modified so that the articular module is formed only with the scaphoid (radial part). The body module would then also be reduced to fit only the radial part of the radius and the spherical ball joint component 26' of the tail module 12' would also be displaced radially as shown, for example, in FIG. 5.

Figure 6:
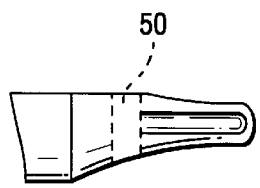
FIG. 6 discloses a variation in the tail module disclosed in FIGS. 1 and 4.

In instances where the only damaged part is the lunate fossa of the radial articular surface, the prosthesis may be modified to be of compact or mono-block construction, holding the articular surface and body and tail parts within the lunar articular surface of the radius, and the ulnar part of the distal radius, fixed with screws and/or cement which cross the body into the bone (see the transverse hole 50 in FIG. 6).

In the designs created for finger joints, the device is composed of the stem and the articular part. The stem fits the medullar cavity of the tubular bones of the hand. Since the articular surface is exactly anatomic, it can be applied as a partial replacement prosthesis without any intervention needed for the healthy opposing particular surface.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A prosthesis system for partial or total articular surface replacement comprising:
   a tail module having one or more grooves at one end thereof and a first ball joint component at an opposite end thereof;
   an articular module, a portion of which has an anatomic shape of a distal radial articular surface, another portion of which is provided with a second ball joint component; and a collar module interposed between said tail module and said articular module, and comprising a pair of sockets adapted to receive the first and second ball joint components of the tail module and articular module.

2. The prosthesis system of claim 1 wherein said collar module is comprised of a pair of half sections held together by a fastener.

3. The prosthesis system of claim 1 wherein one or more of said tail, articular and collar modules have one or more fixation holes therein.

4. The prosthesis system of claim 1 wherein the tail module has one or more grooves therein to prevent movement after insertion.

5. The prosthesis system of claim 1 wherein said articular module has an enlarged end with a threaded hole adapted to receive a holding device for manipulating the articular module.

6. The prosthesis system of claim 1 wherein said tail module, collar module and articular module are constructed of metal.

7. The prosthesis system of claim 1 wherein said tail module, collar module and articular module are constructed of plastic.

* * * * *